United States Patent [19]

Gammill

[11] Patent Number: 4,609,739
[45] Date of Patent: Sep. 2, 1986

[54] SYNTHETIC ROUTES TO BENZOFURANS AND BENZOTHIOPHENES AND INTERMEDIATES THEREFOR

[75] Inventor: Ronald B. Gammill, Portage, Mich.

[73] Assignee: The Upjohn Company, Kalamazoo, Mich.

[21] Appl. No.: 668,765

[22] Filed: Nov. 6, 1984

[51] Int. Cl.$^4$ ................. C07D 307/86; C07D 333/54; C07D 333/24; C07D 307/54
[52] U.S. Cl. ........................................ 549/57; 549/71; 549/471; 549/486
[58] Field of Search ................... 549/57, 71, 471, 486

[56]  References Cited

U.S. PATENT DOCUMENTS 4,284,569  8/1981  Gammill .......................... 260/345.2
4,434,296  2/1984  Gammill .............................. 549/471
4,459,420  7/1984  Gammill .............................. 549/471

OTHER PUBLICATIONS

A. Mustafa, Benzofurans, John Wiley & Sons, Contents & pp. 1–13 (1974).
A. Mustafa, Furopyrans and Furopyrones, Chapter 3, pp. 102–159 (1967).
L. R. Row, et al., Indian J. Chem., 5:505-106 (1967).
R. B. Gammill, et al., J. Org. Chem., 48:3863-3865 (1983).
R. B. Gammill, et al., J. of Med. Chem., 26:1672-1674 (1983).
G. Buchi, et al., J. Org. Chem., 43:3983-3987 (1978).
T. W. Hart, et al., Tet. Lett., 21:2295-2296 (1980).
A. McKillop, et al., J. Org. Chem., 41:282-287 (1976).
M. G. Dolson, et al., J. Am. Chem. Soc., 103:2361-2371 (1981).
F. R. Hewgill, et al., J. Chem. Soc.(C), 12:1556-1558 (1968).
A. E. Ebnother et al., Helv. Chim. Acta., 35:910-928 (1952).
F. Wessely, et al., Monatsh. Chem., 84:124-133 (1953).
F. Wessely, et al., Monatsh. Chem. 83:1253-1273 (1952).
K. Yoshida, et al., J. Org. Chem., 40:3805-3806 (1975).
Loewenthal-Protective Groups in Org. Chemistry, edited by McOmie, Plenum Press (1973), Chapter 9, pp. 323-331, 339,340,350,351,360,361,377-379 & 389.

Primary Examiner—Henry R. Jiles
Assistant Examiner—Bernard I. Dentz
Attorney, Agent, or Firm—Martha A. Cox

[57]  ABSTRACT

The present invention provides novel compositions of matter and processes for their preparation. More particularly, the present invention consists of novel chemical intermediates and associated processes for the preparation of khellin and other furochromone analogues, which have demonstrated antiatherosclerotic activity. These novel intermediates and processes can also be used for the preparation of benzofurans and benzothiophenes which inhibit the synthesis of leukotriene and/or lipoxygenase.

4 Claims, No Drawings

SYNTHETIC ROUTES TO BENZOFURANS AND BENZOTHIOPHENES AND INTERMEDIATES THEREFOR

BACKGROUND OF THE INVENTION

The present invention provides novel compositions of matter and processes for their preparation. Particularly, the present invention relates to novel chemical intermediates and associated processes for the preparation of both known and novel precursors of khellin and other furochromone analogues, which have demonstrated lipid-altering and antiatherosclerotic activity. See. U.S. Pat. No. 4,284,569. Furthermore, these chemical intermediates can be used in the preparation of certain benzofurans and benzothiophenes which have been shown to inhibit the synthesis of leukotrienes and/or inhibit the action of lipoxygenase in mammalian metabolism. See application, Ser. No. 561,601, filed Dec. 14, 1983 now abandoned. The synthesis of the compounds, which are noted herein as D-3 and D-4 is shown herein in Chart D.

Khellin and related compounds are known to exert a wide variety of pharmacological effects. Khellin has been reported to exhibit useful antiatherosclerotic activities. Moreover, numerous analogues of khellin likewise are known to exert useful antiatherosclerotic effects. For example, 7-methylthiomethyl-4,9-dimethoxyfurochromone is described in U.S. Pat. No. 4,284,569 as such a useful antiatherosclerotic substance.

The leukotrienes are a class of unsaturated fatty acid compounds which are derived from arachidonic acid by the action of lipoxygenase. See, e.g., Samuelsson, *Trends in Pharmacological Sciences* 5:227 (1980); Samuelsson et al., *Annu. Rev. Biochem.* 47:997–1029 (1979). For a discussion of leukotriene nomenclature, see Samuelsson et al., *Prostaglandins* 19:645 (1980).

The leukotrienes have been discovered as potent constrictors of human bronchi. That is, certain leukotrienes are mediators of the action of slow-reacting substance of anaphylaxis (SRS-A). See, e.g., Dahlèn, *Nature* 288:484 (1980). These compounds are therefore important mediators of bronchoconstriction in humans.

The role of leukotrienes as agonists in immediate hypersensitivity and other pathological conditions has led to research into inhibitors of leukotriene biosynthesis and leukotriene antagonists. See, e.g., Corey et al., *Tet. Lett.* 21:4243 (1980).

Im mammalian metabolism, arachidonic acid is transformed to 12-L-hydroperoxy-5,8,10,14-eicosatetraenoic acid by the action of 12-lipoxgenase. See Hamberg et al., *Proc. Nat. Acad. Sci.* 71:3400–3404 (1974). Similarly, 5-lipoxygenase transforms arachidonic acid into 5-S-hydroperoxy-6,8,11,14-eicosatetraenoic acid. Thus, an agent which inhibits the action of lipoxygenase would be useful in treating or preventing untoward conditions associated with lipoxygenase products.

Therefore, compounds which inhibit the action of lipoxygenase are useful in the treatment of inflammatory conditions where it is desirable to prevent migration of polymorphonuclear leukocytes to the inflammatory site. They are also useful in the treatment of asthma.

Methods for the total synthesis of khellin and related compounds are known. For example, pyrogallol has been employed as a starting material for the synthesis of furochromones such as khellin. See J. R. Clarke et al., *J. Chem. Soc.* 302 (1949), R. A. Baxter et al., *J. Chem. Soc.* S30 (1949), A. Schonberg et al., *J. Am. Chem. Soc.*, 73:2960 (1951), V. V. S. Murti et al., *Proc. of the Indian Acad. of Sci.* 30A:107 (1949), and T. A. Geissman et al., *J. Am. Chem. Soc.* 73:1280 (1951). Also descriptive of the synthesis of khellin are E. Spath et al., *Chem. Ber.* 71:106 (1938), O. Dann et al., *Chem. Ber.* 93:2829 (1960), O. Dann et al., *Ann. Chem.* 605:146 (1957), and V. V. S. Murti et al., *J. Sci. Ind. Res.* (India) 8B:112 (1949). See also U.S. Pat. No. 2,680,119 describing the synthesis of khellin and related compounds.

Other references describing the synthesis of intermediates useful in the preparation of khellin for analogues include: R. Aneja et al., *Chem. Ber.* 93:297 (1960), R. Aneja et al., *J. Sci. Ind. Res.* (India) 17B:382 (1958), T. S. Gardner et al., *J. Org. Chem.* 15:841 (1950), and L. R. Row et al., *Indian J. Chem.* 5:105 (1967).

Accordingly, the references cited above describe the preparation of 1-(6-hydroxy-4,7-dimethoxy-5-benzofuranyl)-ethanone. Also known is the related compound 6-hydroxy-4,7-dimethoxy-5-benzofurancarboxylic acid, methyl ester, described by C. Musante *Gazz. Chim. Ital.* 88:910 (1958).

One method for the preparation of the lipoxygenase and/or leukotriene-inhibiting benzofurans and benzothiophenes is described in said application, Ser. No. 561,601, filed Dec. 14, 1983.

PRIOR ART

Methods of the total synthesis of khellin are known, as are certain chemical intermediates useful in its synthesis. For example, the total synthesis of furochromones from benzofurans has been accomplished by utilizing a substituted benzene ring from which to synthesize the fused benzofuran ring system. See A. Mustafa, "Benzofurans" (1974) and A. Mustafa, "Furopyrans and Furopyrones, Chapter 3: Furochromones" (1967). Also, pyrogallol has been employed as a starting material for the synthesis of khellin and antiatherosclerotic analogues thereof. See U.S. Pat. No. 4,459,420. See also L. R. Row, et al., *Indian J. Chem.* 5:105 (1967).

U.S. Pat. No. 4,434,296 provides a method whereby 3-furoic acid is transformed to the benzofuran intermediates useful in the synthesis of khellin and khellin analogues. In this method, 3-furoic acid is converted to an enaminone diester, which undergoes Dieckmann cyclization to yield a highly functionalized benzofuran. Methylation, Baeyer-Villager oxidation and conversion of the resulting hydroxy ester to khellinone and then khellin completes this synthesis. See R. B. Gammill and B. R. Hyde, *J.Org.Chem.* 48:3863 (1983). See also R. B. Gammill, C. E. Day, and P. E. Schurr, *J. of Medicinal Chem.* 26:1672 (1983); U.S. Pat. No. 4,284,569.

The present invention present a new 3-furoic acid route to khellin. One of the most important steps of the present invention is the oxidation of the methyl ketone to the intermediate quinone monoketal using thallium (III) nitrate or lead (IV) acetate.

Most of the previous reports of the oxidation of p-methoxyphenols to benzoquinone monoketals have relied on 2,3-dichloro-5,6-dicyanobenzoquinone, thallium (III) nitrate, and ferric chloride as the oxidants. See G. Buchi et al., *J. Org. Chem.* 43:3983 (1978). The use of thallium (III) nitrate to oxidize p-methoxyphenols containing a carbonyl or carboxyl function ortho- to the phenolic hydroxyl has been reported by Hart and Scheinmann. See T. W. Hart and F. Scheinmann, *Tet. Lett.* 21:2295 (1980). Oxidation of 2-formyl-4-methoxyacetophenone with thallium (III) nitrate afforded the quinone monoketal in which the aldehyde was also transformed to an acetal. No yield was reported for this oxidation. Similar treatment of 2-carbomethoxy-4-methoxyphenol afforded the methoxyl-substituted quinone monoketal in 97% yield as a crystalline solid.

For the thallium (III) nitrate oxidation of a system that yielded an ortho-quinone monoketal, see A. McKillop et al., *J. Org. Chem.* 41:282 (1976). For an example of an anodic oxidation to yield an ortho-quinone monoketal, see M. G. Dolson and J. S. Swenton, *J. Am. Chem.-Soc.* 103:2361 (1981).

F. R. Hewgill and S. L. Lee, *J. Chem. Soc.* 1556 (1968), report the oxidation of alkoxyphenols using lithium (IV) acetate and report the isolation of 2,5-di-t-butyl-1,4-benzoquinone by methanol recrystallization. A. E. Brother, T. M. Meijer, and H. Schmid., *Helv. Chim. Acta.* 35:910 (1952); F. Wessely and J. Kotlan, *Monatsh. Chem.* 84:124 (1953); F. Wessely and L. Holzer, *Monatsh. Chem.* 83:1253 (1952) disclose the preparation of quinol diacetates using lead (IV) acetate. Anodic acetoxylation of dimethoxybenzenes is disclosed in K. Yoshida et al., *J. Org. Chem.* 40:3805 (1975).

SUMMARY OF THE INVENTION

The present invention particularly provides:
(1) A process for preparing a compound of formula IV, wherein X is —O— or —S—, which comprises: cyclizing the compound of formula III using a Dieckmann-type cyclization.
(2) A process for preparing a compound of formula VII, which comprises:
   (a) oxidizing a compound of formula VI with a compound selected from the group consisting of thallium (III) nitrate trihydrate and lead (IV) acetate, in methanol;
   (b) reacting the product obtained in step (a) with allyl alcohol; and
   (c) treating the product obtained in step (b) with acid.
(3) A process for preparing a compound of formula IX, which comprises:
   (a) oxidizing a compound of formula VI with a compound selected from the group consisting of thallium (III) nitrate trihydrate and lead (IV) acetate in methanol; and
   (b) treating the product obtained in step (a) with acid.
(4) A compound of formula III, wherein X is —O— or —S—.
(5) A compound of the formula X
   wherein $R_1$ is
   (a) —OH,
   (b) =O, or
   (c) —OCH$_3$;
      wherein $R_2$ is —C(O)R$_5$;
   wherein $R_3$ is
   (a) —H,
   (b) —OCH$_3$, or
   (c) —OCH$_2$—CH=CH$_2$;
   wherein $R_4$ is
   (a) —H, or
   (b) —OCH$_3$;
   wherein $R_5$ is (C$_1$–C$_9$) alkyl; wherein P, Q, and T are single or double bonds; with the provisos that:
   (1) P and T are both double bonds and Q is a single bond when $R_3$ is —OCH$_2$—CH=CH$_2$ and $R_4$ is hydrogen;
   (2) P is a double bond and Q and T are both single bonds when $R_3$ and $R_4$ are both =OCH$_3$; and
   (3) Q is a double bond and P and T are both single bonds when $R_3$ is hydrogen and $R_4$ is other than hydrogen.
(6) A compound of the formula XI wherein X is
   (a) —S— or
   (b) —O—;
      wherein $R_2$ is
   (a) —CO$_2$CH$_3$,
   (b) —CO$_2$H, or
   (c) —C(O)R$_5$;
      wherein $R_5$ is (C$_1$–C$_4$)alkyl.

The carbon atoms content of various hydrocarbon-containing moieties is indicated by a prefix designating the minimum and maximum number of carbon atoms in the moiety, i.e., the prefix (C$_i$–C$_j$) indicates a moiety of the integer "i" of the integer "j" carbon atoms, inclusive. Thus, for example, (C$_1$–C$_3$) alkyl refers to alkyl of one to three carbon atoms, inclusive, or methyl, ethyl, propyl, and isopropyl.

Examples of alkyl of one to nine carbon atoms, inclusive, are methyl, ethyl, propyl, butyl, pentyl, hexyl, heptyl, octyl, and nonyl, and isomeric forms thereof.

The compounds of the present invention will be named herein using the Chemical Abstracts numbering system (see "Naming and Indexing of Chemical Substances for Chemical Abstracts during the Ninth Collective Period (1972-1976)," a reprint of section IV from the Volume 76 Index Guide). When X is —O— and —S—, the compounds of this invention are named as benzofurans and benzothiophenes, respectively.

The process of the present invention is more completely understood by reference to the charts below. In these charts, X is as defined above, and in Chart D, R is defined as (C$_1$–C$_9$)alkyl.

Chart A herein describes the method by which several novel intermediates to khellin and its analogues are prepared. Charts B and C herein describe two methods by which khellin is prepared from the intermediates obtained in Chart A. Chart D herein describes the method by which compounds with proven leukotriene and/or lipoxygenase-inhibiting activity are prepared from the intermediates obtained in Chart A.

With respect to Chart A, the dianion of the formula A-1 compound, 3-furoic acid, is transformed to the formula A-2 keto diester by treatment with succinic anhydride, followed by esterification of the crude diacid. This method is described more fully in R. B. Gammill and B. R. Hyde, *J. Org. Chem.* 48:3863 (1983).

Thereafter, the formula A-2 keto diester is converted to the novel formula A-3 ketal. This ketalization does not proceed under normal ketalization conditions (i.e., catalytic para-toluenesulfonic acid/ethene glycol/benzene). The formula A-2 keto diester is treated with trimethylorthoformate, methanol, and para-toluenesulfonic acid at reflux to afford the formula A-3 ketal in high yield. The oxygen analogue of the formula A-3 compound requires more refluxing time than does the sulfur analogue. This procedure is a modification of the procedure developed by Glatz et al., *J. Am. Chem. Soc.* 101:2171 (1979), and is described more fully in Example 2.

The formula A-3 ketal is cyclized to afford the novel benzofuran/benzothiophene ester of formula A-4. This Dieckmann-type cyclization proceeds in the presence of potassium tert-butoxide in tetrahydrofuran at −80° to 0° C. and is followed by acid treatment (preferably anhydrous hydrochloric acid) to yield the fully substituted and oxygen-differentiated benzofuran/benzothiophene of formula A-4. This cyclization, known as a Dieckmann condensation, represents a new method for the synthesis of highly functionalized benzofurans/benzothiophenes and provides methodology for the construction of an aromatic ring onto an existing furan ring. See R. B. Gammill and B. R. Hyde, *J. Org. Chem.* 48:3863–5 (1983). For a review of prior methods, see A. Mustafa, *The Chemistry of Heterocyclic Compounds*, Vol. 29 (1979); J. P. Schaefer, *Organic Reactions* 15:1–203 (1967).

The formula A-4 ester is hydrolyzed (e.g., using lithium hydroxide in aqueous tetrahydrofuran) to yield the formula A-5 acid. Lithium hydroxide is the preferred hydrolyzing agent as attempts to hydrolyze the formula A-4 ester with sodium hydroxide, barium hydroxide or potassium hydroxide, all gave lower yields of the formula A-5 acid. The carboxylic acid of formula A-5 is converted to the formula A-6 methyl ketone by standard methodology (e.g., treatment of the formula A-5 acid with methyl lithium in tetrahydrofuran at 0° C. for 4 hours).

Charts B and C provide alternative methods by which khellin (formula B-8 (C-8)) is prepared from the formula A-6 methyl ketone of Chart A.

In accordance with the procedure of Chart B, the formula A-6 compound of Chart A is employed as the formula B-1 starting material. This formula B-1 compound is oxidized with a compound selected from the group consisting of lead (IV) acetate and thallium (III) nitrate trihydrate, in a $C_1$–$C_4$ alkanol solvent, (preferably, methanol with at least 5% trimethylorthoformate or a 1:1 mixture of methanol and trimethylorthoformate), to afford the formula B-2 novel intermediate quinone monoketal. These are the preferred oxidizing agents since sodium periodate, E. Alder and B. Berggren, *Acta. Chem. Scand.* 14:529 (1960), 2,3-dichloro-5,6-dicyanobenzoquinone, G. Buchi et al., *J. Org. Chem.* 43:3983 (1978), dimethylformamide complex of ferric chloride, S. Tobinaga and E. Kotani, *J. Am. Chem. Soc.* 94:309 (1972), and ceric ammonium nitrate, W. Durkheimer and L. A. Cohen, *Biochemistry* 3:1948 (1964), all failed to induce the above oxidation.

Under the acidic conditions of the oxidation, the formula B-2 intermediate rapidly adds methanol to yield the Michael adduct of formula B-3. The formula B-3 compound is treated with excess allyl alcohol at reflux and then with acid (e.g., anhydrous acid or a hydrated acid in an organic solvent) to give a compound of the formula B-5. See description of procedure in Example 6.

Methylation of the formula B-5 compound (e.g., using dimethyl sulfate/potassium carbonate/1,4,7,10,13,16-Hexaoxacyclooctadecane [also known as 18-crown-6]/tetrahydrofuran/reflux) yields the novel bensofuran of the formula B-6. See R. B. Gammill and B. R. Hyde, *J. Org. Chem.* 48:3863–5 (1983).

Treatment of the formula B-6 compound with a Lewis acid (e.g., anhydrous hydrogen bromide or boron trifluoride etherate in methylene chloride, and aluminum chloride in nitrobenzene) at −15° C. for 15 minutes results in the selective removal of the allyloxy group to yield the formula B-7 compound, which is known as khellinone.

The formula B-7 compound is then converted to khellin by Claisen condensation/acid-catalyzed cyclodehydration. This procedure is more fully described in U.S. Pat. No. 4,284,569.

In accordance with the procedure of Chart C, the formula A-6 compound of Chart A is employed as the formula C-1 starting material. This formula C-1 compound is oxidized using a compound selected from the group consisting of thallium (III) nitrate trihydrate or lead (IV) acetate, in a $C_1$–$C_4$ alkanol solvent (e.g., preferably, methanol with at least 5% trimethylorthoformate or a 1:1 mixture of methanol and trimethylorthoformate) to afford the formula C-2 intermediate quinone monoketal. See Example 7. Under the acidic conditions of the oxidation, the formula C-2 intermediate rapidly adds methanol to the enone double bond to yield the formula C-3 adduct.

Treatment of the formula C-3 intermediate with acid (e.g., anhydrous acid or a hydrated acid in an organic solvent) effects the elimination of methanol to yield the formula C-5 compound.

Methylation of the formula C-5 compound (e.g., using dimethyl sulfate/potassium carbonate/1,4,7,10,13,16-Hexaoxacyclooctadecane [18-crown-6]/tetrahydrofuran/reflux), as in the conversion of the formula B-5 compound of the formula B-6 compound above, yields the formula C-6 compound. A similar procedure is described in R. B. Gammill and B. R. Hyde, *J. Org. Chem.* 48:3863–5 (1983).

Three alternative routes from the formula C-6 compound to the C-7 compound, which is known as khellinone, include: (1) Treatment of the formula C-6 compound with anhydrous hydrogen bromide in chloroform at elevated temperatures to afford a mixture of the formula C-7 compound, khellinone, and the formula C-5 compound. (2) Treatment of the formula C-6 compound with boron trifluoride etherate in methylene chloride at room temperature to afford the formula C-7 compound as the major product and the formula C-5 compound, as the minor product. (3) Treatment of the formula C-6 compound in methylene chloride with a nitrobenzene solution of aluminum chloride to afford the formula C-7 compound as the sole product.

The formula C-7 compound is then converted to khellin by Claisen condensation/acid-catalyzed cyclodehydration. This procedure is more fully described in U.S. Pat. No. 4,284,569.

As noted above, the compounds khellin and khellinone may be prepared. See formulas I and II. Khellinone is known to be useful in the preparation of a wide variety of antiatherosclerotic substances, like khellin and its analogues. See U.S. Pat. No. 4,284,569. Accordingly, the manner of the preparation and pharmacological use of these compounds are incorporated herein by refernce from the description of their preparation and use in U.S. Pat. No. 4,284,569.

Chart D depicts the preparation of the leukotriene and/or lipoxygenase-inhibiting compounds from the intermediates obtained in Chart A. In accordance with the procedure of Chart D, the formula A-5 compound of Chart A is employed as the formula D-1 starting material. The formula D-1 carboxylic acid is treated with an alkyl lithium (e.g., ethyl lithium, propyl lithium, and butyl lithium) in an ether solvent (e.g., ethyl ether, tetrahydrofuran, and dioxane) at or below room temperature and in an inert atmosphere (e.g. nitrogen and argon) to afford the alkyl ketone of formula D-2. The reaction is quenched with a saturated solution of ammonium chloride and extracted with an organic solvent (e.g., ethyl ether, ethyl acetate, and toluene). See M. J.

Jorgenson, *Organic Reactions* 18:1–98 (1970); see also B. J. Wakefield, *The Chemistry of Organolithium Compound* (1974). This reaction was used above to convert the acid of formula A-5 to the methyl ketone of formula A-6 in the total synthesis of khellin.

The carbonyl group of the alkyl ketone of formula D-2 is reduced to afford the compound of formula D-3. Amalgamated zinc in concentrated hydrochloric acid, water and an inert solvent (e.g., ethanol and toluene) are added to the compound of formula D-2, and the mixture heated to reflux. The reaction is worked up by extracting with an organic solvent (e.g., toluene and ethyl acetate) and removing that solvent, in vacuo. See R. R. Read, and J. Wood, *Organic Synthesis* 3:444 (1955); M. S. Newman, W. C. Sagar, and C. C. Cochrane, *J. Org. Chem.* 23:1832 (1958).

The hydroxyl group of the compound of formula D-3 is acylated with a mixture of acetic anhydride and pyridine at room temperature for several hours. Removal of the solvents affords the compound of formula D-4. See said Ser. No. 561,601, filed Dec. 14, 1983.

As described above, the formula A-5 compound of this invention may be used to prepare a wide variety of benzofurans and benzothiophenes, which are useful as leukotriene and/or lipoxygenase inhibitors. Accordingly, the manner of the preparation and pharmacological use of these compounds are incorporated herein by reference from the description of their preparation and use in said Ser. No. 561,601, filed Dec. 14, 1983.

DESCRIPTION OF THE PREFERRED EMBODIMENTS

The preparation of the novel benzofurans and benzothiophenes of the instant specification are more readily understood by the following examples:

EXAMPLE 1

A. 2-furanbutanoic acid, 3-(methoxycarbonyl)-α-oxomethyl ester (formula A-2: X is oxygen)

Refer to Chart A

Raid addition of succinic anhydride (1.1 equiv./tetrahydrofuran) to the dianion of 3-furoic acid of formula A-1 (2 equiv. of lithium diisopropyl amide/tetrahydrofuran/−78° C.) followed by esterification (hydrochloric acid/methanol or diazomethane/chloroform) of the crude diacid yields, after chromatography (silica gel, 5% ethyl acetate/chloroform), the title product as a colorless oil.

B. 2-Thiophenebutanoic acid, 3-(methoxycarbonyl)-α-oxo-/methyl ester (formula A-2: X is sulfur)

Refer to Chart A

3-Thiophene carboxaldehyde is oxidized (Ag$_2$O/H$_2$O) to 3-thiophene carboxylic acid of formula A-1. Treatment of the acid with lithium diisopropyl amide (2.2 equiv./tetrahydrofuran/−78° C.) affords a pale yellow dianion which, upon treatment with succinic anhydride (1.1 equiv./tetrahydrofuran), followed by esterification (hydrochloric acid/methanol or diazomethane/chloroform), yields the title product.

EXAMPLE 2

A. 2-Furanbutanoic Acid, α,α-dimethoxy-3-(methoxycarbonyl)-, methyl ester (Formula A-3: X is oxygen)

Refer to Chart A

The formula A-2 product of Example 1(A) (25.08 g), trimethylorthoformate (55.38 g), para-toluensulfonic acid (1.5 g) and methanol (200 ml) are heated at reflux for 48 hours. Pyridine (5 ml) is added, and the excess methanol and trimethylorthoformate removed in vacuo. The resulting oil is chromatographed over silica gel (1 kg, 25% ethyl acetate/hexane) to yield 25.16 g of the title product as a colorless oil.

Physical characteristics are as follows:

IR (cm$^{-1}$, film): 3140, 3120, 1735, 1585, 1510, 1290, 1195, 1165, 1110, 1070, 1055, 1030, 880 and 755.

$^1$H-NMR (δ, CDCl$_3$): 7.4, 6.7, 3.85, 3.6, 3.3 and 2.1–3.8.

Mass spectra (m/e): 286, 255, 223, 200, 199, 196, 195, 163, 153, 137 and 59.

UV (λ$_{max}$, ethanol): 238.

Anal. Calc'd. for C$_{13}$H$_{18}$O$_7$: C, 54.54; H, 6.29. Found: C, 54.36; H, 6.21.

B. Methyl-α,α-dimethoxy-3-methoxycarbonyl-2-thiophenebutanoate (Formula A-3: X is sulfur)

Refer to Chart A

The formula A-2 product of Example 1(B) (10.0 g, 39.0 ml), trimethylorthoformate (20.67 g), para-toluensulfonic acid (1.0 g) and methanol (100 ml) are refluxed under nitrogen for 8 hours. Additional trimethylorthoformate (approx. 15 g) is added and refluxing continued for 36 hours until the reaction is complete. After cooling the reaction to room temperature, pyridine (3 ml) is added and the excess methanol and trimethylorthoformate removed in vacuo. The resulting oil is chromatographed over 700 g of silica gel (230–400 mesh, 25% ethyl acetate/Skellysolve-B, [a commercially-available mixture of essentially n-hexane]) to yield 11.60 g of the title product as a colorless oil.

Physical characteristics are as follows:

IR (cm$^{-1}$, mull): 2950, 1735, 1708, 1437, 1285, 1267, 1194 and 1127.

$^1$H-NMR (δ, CDCl$_3$): 7.40, 7.28, 3.80, 3.55, 3.15, 2.65 and 2.15.

Mass spectra (m/e): 302, 271, 239, 217, 216, 215, 211, 179, 169, 139 and 59.

UV (λ$_{max}$, ethanol): 244.

Anal. Calc'd. for C$_{13}$H$_{18}$O$_6$S: C, 51.65; H, 5.96; S, 10.59. Found: C, 51.99; H, 5.93; S, 10.68.

EXAMPLE 3

A. 5-Benzofurancarboxylic acid, 4-hydroxy-7-methoxy-, methyl ester Formula A-4: X is oxygen)

Refer to Chart A

Potassium tert-butoxide (72.4 g) is dissolved in tetrahydrofuran (8.0 l) and cooled to −78° C. under an atmosphere of nitrogen. The formula A-3 product of Example 2(A) (84.0 g), also in tetrahydrofuran (250 ml), is added dropwise over 30 minutes. After stirring for 1.25 hours at −78° C., anhydrous hydrochloric acid is bubbled into the reaction mixture until the solution becomes transparent yellow. The cooling bath is removed and stirring is continued for 1 hour. Evaporation at 40° C., in vacuo, affords 78.3 g of crude solid. The product is purified by gravity-flow chromatography over 3.0 kg of silica gel. Elution with 50% ethyl acetate/Skellysolve-B affords 62.9 g of the title product as a white solid.

Physical characteristics are as follows:
Melting point: 127.8°–128.8° C.
IR (cm$^{-1}$, mull): 1361, 2927, 1479, 1203, 1666, 1069, 1450, 2949 and 1232.
$^1$H-NMR ($\delta$, CDCl$_3$): 11.0, 7.55, 7.1, 6.9 and 3.9.
Mass spectra (m/e): 222, 191, 190, 175, 163, 162, 147, 134, 119 and 53.
Anal. Calc'd. for C$_{11}$H$_{10}$O$_5$: C, 59.45; H, 4.50. Found: C, 59.10; H, 4.60.
Silica Gel thin-layer chromatography: R$_f$=0.72 in 5% ethyl acetate/chloroform.

B. Benzo(b)thiophene-5-carboxylic acid, 4-hydroxy-7-methoxy-, methyl ester. (Formula A-4: X is sulfur)

Refer to Chart A

Potassium tert-butoxide (82.9 g) is dissolved in tetrahydrofuran (8.0 l) in a flame-dried 12-liter flask, under an atmosphere of nitrogen. The formula A-3 product of Example 2(B) (102.0 g), also in tetrahydrofuran (150 ml), is added dropwise over 1 hour. After stirring for 2 hours at −78° C., anhydrous hydrochloric acid is bubbled into the reaction mixture until the solution becomes transparent yellow. After evaporation at 50° C., in vacuo, the residue is triturated with methylene chloride (2 l) and the solid is filtered and discarded. The methylene chloride solution is filtered through a pad of magnesium sulfate and evaporated to afford 49.5 g of the title product.

Alternatively, potassium tert-butoxide (17.20 g) is dissolved in tetrahydrofuran (300 ml) and cooled to −78° C. under an atmosphere of nitrogen. The formula A-3 product of Example 2(B) (11.60 g), also in tetrahydrofuran (200 ml), is added dropwise over 20 minutes. The dry ice/acetone bath is removed and stirring continued for 1.5 hours. The reaction is quenched by addition of 2N hydrochloric acid (approx. 200 ml), which is extracted three times with ether. The combined extracts are dried over magnesium sulfate and the solvent removed, in vacuo, to yield a tan solid (9.3 g). The solid is chromatographed over 300 g of Florisil (1% ethyl acetate/methylene chloride) to yield 8.3 g of the title product as a white solid.

Physical characteristics are as follows:
Melting point: 139.4°–140.1° C.
IR (cm$^{-1}$, mull): 2958, 2926, 2854, 1666, 1449, 1431, 1358, 1266, 788 and 760.
$^1$H-NMR ($\delta$, CDCl$_3$): 11.25, 7.65, 7.40, 7.10 and 3.90.
Mass spectra (m/e): 239, 238, 208, 207, 206, 191, 178, 163 and 135.
UV ($\lambda_{max}$, ethanol): 229, 234, 241, 250, 279, 289, 339 and 349.
Anal. Calc'd. for C$_{11}$H$_{10}$O$_4$S: C, 55.46; H, 4.20; S, 13.44. Found: C, 55.30; H, 4.28; S, 13.15.

EXAMPLE 4

A. 4-Hydroxy-7-methoxybenzo(b)furan-5-carboxylic acid (Formula A-5: X is oxygen)

Refer to Chart A

The formula A-4 product of Example 3(A) (12.1 g) is dissolved in tetrahydrofuran (100 ml). Lithium hydroxide (5.0 g), dissolved in boiling distilled water (25 ml), is added at room temperature and the solution brought to reflux for 2.5 hours. The reaction mixture is cooled to 0° C., and ice (approx. 100 ml) and concentrated hydrochloric acid are added to a pH of 1. The resulting gray precipitate is filtered, air-dried overnight and dried in vacuo for 2 days to yield 11.1 g of impure title product. 2.0 g of this product is applied to silica gel (200 g) and eluted with ethyl acetate to afford 1.65 g of light gray crystals. Recrystallization from ethyl acetate gives 1.4 g of the title product as a white solid.

Physical characteristics are as follows:
Melting point: 192°–195° C.
IR (cm$^{-1}$, mull): 1215, 1305, 1453, 2925, 1478, 1281, 1067, 1606, 1462, 1646 and 2953.
$^1$H-NMR ($\delta$, dimethylsulfoxide): 7.60, 7.30 and 3.95.
Mass spectra (m/e): 208, 191, 190, 175, 162, 147, 134, 119, 63 and 53.
UV ($\lambda_{max}$, ethanol): 224, 255 and 317.
Anal. Calc'd for C$_{10}$H$_8$O$_5$: C, 57.69; H, 3.87. Found: C, 57.77; H, 4.01.

B. Benzo(b)thiophene-5-carboxylic acid, 4-Hydroxy-7-methoxy (Formula A-5: X is sulfur)

Refer to Chart A

The formula A-4 product of Example 3(B) (16.4 g) is dissolved in hot tetrahydrofuran (100 ml). Water (20 ml) and lithium hydroxide (15.0 g) are added and the solution heated at reflux for 10 hours. The reaction mixture is cooled to 50° C. and the tetrahydrofuran removed in vacuo. The resulting aqueous solution is diluted with water (to 500 ml) and cooled below room temperature with an ice bath, while concentrated hydrochloric acid is added to a pH of 1. The resulting precipitate is collected on a filter. The wet crystals are dissolved in ethyl acetate, dried over magnesium sulfate and the solvent removed, in vacuo, to yield 15.3 g of the crude title product. Recrystallization from acetonitrile yields 12.8 g of the title product.

Physical characteristics are as follows:
Melting point: 205°–208° C.
IR (cm$^{-1}$, mull): 2926, 2867, 2854, 1641, 1503, 1449, 1443, 1417, 1245 and 688.
$^1$H-NMR ($\delta$, dimethylsulfoxide): 7.75, 7.20 and 3.95.
Mass spectra (m/e): 225, 224, 207, 206, 191, 178, 163, 150, 135 and 103.
UV ($\lambda_{max}$, ethanol): 225, 271, 275, 289 and 337.
Anal. Calc'd. for C$_{10}$H$_8$O$_4$S: C, 53.56; H, 3.60; S, 14.30. Found: C, 53.66; H, 3.80; S, 14.34.

EXAMPLE 5

A. Ethanone, 1-(4-Hydroxy-7-methoxy-5-benzofuranyl)-(Formula A-6: X is oxygen.)

Refer to Chart A

The formula A-5 product of Example 4(A) (8.32 g) is dissolved in tetrahydrofuran (250 ml) under an atmosphere of nitrogen and then cooled to 0° C. Methyl lithium (107 ml of 1.5M) is added dropwise over 3 hours and the solution stirred an additional 4 hours at 0° C. The reaction is quenched with saturated ammonium chloride (250 ml) and extracted three times with 100 ml of ether. The combined organic extracts are dried over magnesium sulfate and the solvent removed, in vacuo, to yield 7.22 g of crude title product. Chromatography over 500 g of silica gel (240–400 mesh, 25% ethyl acetate/Skellysolve-B) yields 4.15 g of the pure title product.

Physical characteristics are as follows:

Melting point: 102°–104° C.

IR(cm$^{-1}$, mull): 2925, 2954, 2855, 2860, 1478, 1368, 1606, 1373, 1469 and 1311.

$^1$H-NMR ($\delta$, CDCl$_3$): 7.3, 7.05, 6.90, 3.90 and 2.55.

Mass spectra (m/e): 207, 206, 192, 191, 188, 173, 163, 145, 53 and 43.

UV ($\lambda_{max}$, ethanol): 228, 233, 247, 270 and 348.

Anal. Calc'd. for C$_{11}$H$_{10}$O$_4$: C, 64.07; H, 4.89. Found: C, 64.00; H, 5.04.

B. Ethanone, 1-(4-Hydroxy-7-methoxybenzo(b)thien-5-yl) (Formula A-6: X is sulfur.)

Refer to Chart A

The formula A-5 product of Example 4(B) (11.2 g) is dissolved in tetrahydrofuran (350 ml) under an atmosphere of nitrogen and then cooled to 0° C. Methyl lithium (1.25M, 160 ml) is added dropwise over 2.5 hours and the solution stirred an additional 4 hours (0°–15° C.). The reaction is diluted with saturated ammonium chloride (250 ml) and extracted three times with 100 ml of ether. The combined organic extracts are dried over magnesium sulfate and the solvent removed, in vacuo, to yield 11.35 g of crude title product. Chromatography over 750 g of silica gel (240–400 mesh, 100% ethyl acetate) yields 10.4 g of the title product.

Physical characteristics are as follows:

Melting point: 131.8°–132.2° C.

IR (cm$^{-1}$, mull): 2952, 2925, 2869, 2855, 1618, 1427, 1372, 1326, 816, 721 and 715.

$^1$H-NMR ($\delta$, CDCl$_3$): 7.75, 7.50, 6.90, 4.00 and 2.70.

Mass spectra (m/e): 223, 222, 208, 207, 204, 189, 179, 161, 108 and 43.

UV ($\lambda_{max}$, ethanol): 233, 239, 254, 281, 289 and 366.

Anal. calc'd. for C$_{11}$H$_{10}$O$_3$S: C, 59.44; H, 4.54; S, 14.43. Found: C, 59.53; H, 4.72; S, 14.33.

EXAMPLE 6

5-Acetyl-5,6-dihydro-6,7,7-trimethoxy-4(7H)benzofuranone (Formula B-3 (C-3))

Refer to Charts B and C

The benzofuran ketone of formula A-6 (B-1) (C-1) of Example 5(A) (6.18 g) is dissolved in 300 ml of 50% methanol/trimethylorthoformate and the solution is cooled to 0° C. Thallium trinitrate trihydrate (18.4 g) is dissolved in 150 ml of 50% methanol/trimethylorthoformate and added dropwise to the ketone solution. After stirring for four hours at 0° C., the reaction mixture is allowed to settle and the clear supernate is decanted into a stirred mixture of methylene chloride (2 l) and saturated aqueous sodium bicarbonate (500 ml). The white solid residue is washed three times with 50 ml of methylene chloride and the washings are combined with the work-up mixture. The layers are separated and the aqueous phase is extracted three times with 100 ml of methylene chloride. The organic phases are combined and washed with saturated sodium bicarbonate (500 ml), dried over magnesium sulfate and evaporated at 40° C. in vacuo and then at 0.5 torr. Crystals are formed under vacuum and the yield is 6.98 g of the title product. One gram of the crude product is recrystallized twice from 2.5 ml of ethyl acetate to afford analytically pure material.

Physical characteristics are as follows:

Melting point: 113.2°–115° C.

Silica gel thin-layer chromatography: R$_f$=0.18 in 25% ethyl acetate/Skellysolve-B.

IR (cm$^{-1}$, CHCl$_3$): 1615, 1570, 1455, 1390, 1145, 1095, 1080, and 845.

$^1$H-NMR ($\delta$, CDCl$_3$): 15.63, 7.45, 6.75, 4.47, 3.53, 3.22, 3.16, and 2.25.

UV ($\lambda_{max}$): 208, 218, 264, and 318.

Mass spectra (m/e): 268, 253, 211, 206, 191, 179, 153, 141, 43, and 28.

Anal. calc'd. for C$_{13}$H$_{16}$O$_6$: C, 58.20; H, 6.01. Found: C, 57.86; H, 6.01.

EXAMPLE 7

4(7H)-Benzofuranone, 5-acetyl-7,7-dimethoxy (Formula B-2 (C-2))

Refer to Charts B and C

A solution of thallium trinitrate trihydrate (18.65 g) in a 1:1 mixture of methanol/trimethylorthoformate (150 ml) is added dropwise to a solution of the formula A-6 (B-1) (C-1) product of Example 5(A) in a 1:1 mixture of methanol/trimethylorthoformate (300 ml) at 0° C. After stirring for 4 hours at 0° C., the reaction mixture is allowed to settle and the clear supernate is decanted into a stirred mixture of methylene chloride (2 l) and saturated aqueous sodium bicarbonate (500 ml). The white solid residue is washed three times with 50 ml of methylene chloride and the washings are combined with the workup mixture. The layers are separated and the aqueous phase is extracted three times with 100 ml of methylene chloride. The organic layers are combined, dried over sodium sulfate and filtered. The solvents are removed, in vacuo, at 40° C. to afford a brown oil. The oil is applied to Florisil (100 g) and eluted with 50% ethyl acetate/Skellysolve-B to afford 2.1 g of the title product.

Physical characteristics are as follows:

Melting point: 58°–64° C.

IR (cm$^{-1}$, mull): 3140, 2948, 1696, 1674, 1365, 1069, 1048, 1037, 898, and 765.

$^1$H-NMR ($\delta$, CDCl$_3$): 7.54, 7.25, 6.79, 3.47, and 2.57.

UV ($\lambda_{max}$, ethanol): 206, 218, 264, and 316.

Mass spectra (m/e): 236, 221, 208, 206, 205, 193, 177, 114, and 43.

Anal. Calc'd. for C$_{12}$H$_{12}$O$_3$: C, 61.01; H, 5.12. Found: C, 61.16; H, 5.16.

Alternatively, the formula B-3 (C-3) product of Example 6 (0.25 g) is heated to 110° C. under oil pump vacuum (approximately 0.5 torr) for twenty minutes. The crude product (0.24 g) is recrystallized from ethyl acetate (1.5 ml) to afford 0.175 g of the title product.

Physical characteristics are as follows:

Melting point: 62°–64.2° C.

Silica gel thin-layer chromatography: R$_f$=0.25 in 25% ethyl acetate/Skellysolve-B.

Spectral and analytical data are consistent with those reported above.

EXAMPLE 8

Ethanone, 1-(4-Hydroxy-7-methoxy-6-(2-propenyloxy)-5-benzofuranyl) (Formula B-5)

Refer to Chart B

The formula A-6 (B-1) product of Example 5(A) (2.06 g) is dissolved in a 1:1 mixture of methanol/trimethylorthoformate (500 ml) and cooled to 0° C. Thallium trinitrate trihydrate (6.22 g, in 50 ml of a 1:1 mixture of methanol/trimethylorthoformate) is added to that mixture dropwise over 10 minutes. The reaction is stirred for 5.5 hours and then poured into a mixture of methylene chloride and saturated sodium bicarbonate (350 ml/100 ml) with vigorous stirring. The organic layer is separated, dried over sodium sulfate and solvent removed, in vacuo, to yield 2.52 g of crude adduct of formula B-3. This material is dissolved in allyl alcohol (15 ml) and heated at reflux for 1.5 hours. The reaction is diluted with methylene chloride and 0.2 ml of a saturated hydrochloric acid solution of methylene chloride is added. The solution is stirred for 30 minutes and the solvent removed, in vacuo. Chromatography (silica gel, 10% ethyl acetate/Skellysolve-B) yields 1.29 g of the title product as a yellow oil.

Physical characteristics are as follows:

IR (cm$^{-1}$, film): 1632, 1465, 1437, 1391, 1365, 1348, 1291, 1127, 1061 and 972.

$^1$H-NMR ($\delta$, CDCl$_3$): 9.48, 7.55, 6.96, 6.20, 5.40, 4.72, 4.02 and 2.72.

Mass spectra (m/e): 262, 221, 206, 203, 193, 173 and 163.

UV ($\lambda_{max}$, ethanol): 238, 252, 271, 281 and 352.

Anal. calc'd. for C$_{14}$H$_{14}$O$_5$: C, 64.11; H, 5.38. Found: C, 64.28; H, 5.46.

Alternatively, the benzofuran ketone quinone monoketal of formula B-2 of Example 7 (0.25 g) is dissolved in methylene chloride (1.0 ml) and allyl alcohol (0.12 g) is added at room temperature. Camphorsulfonic acid (0.025 g) is added and the solution immediately turns yellow. After standing for 0.5 hour, the crude title product is chromatographed over silica gel (15 g, 25% ethyl acetate/Skellysolve-B).

The title product (0.09 g) corresponds to those above by thin-layer chromatography (25% ethyl acetate/Skellysolve-B), $^1$H-NMR, and mass spectroscopy.

EXAMPLE 9

Ethanone, 1-(4,7-dimethoxy-6(2-propenyloxy)-5-benzofuranyl) (Formula B-6)

Refer to Chart B

The formula B-5 product of Example 8, potassium carbonate (2.5 g), 1,4,7,10,13,16-hexaoxacyclooctadecane (18-crown-6) (0.2 g), and dimethyl sulfate (0.75 g) are added to tetrahydrofuran and the mixture heated at reflux for 30 minutes. The reaction is cooled to room temperature and solvent removed, in vacuo. The crude reaction is applied directly to a silica gel column (120 g) which, after elution with 50% ethyl acetate/Skellysolve-B, affords 1.1 g of the title product as a colorless oil.

Physical characteristics are as follows:

IR (cm$^{-1}$, film): 1706, 1479, 1433, 1423, 1354, 1346, 1267, 1137, 1070 and 988.

$^1$H-NMR ($\delta$, CDCl$_3$): 7.60, 6.90, 6.15, 5.30, 4.65, 4.05, 3.95 and 2.50.

Mass spectra (m/e): 276, 235, 220, 207, 190, 177, 175, 119 and 43.

UV ($\lambda_{max}$, ethanol): 214, 239 and 290.

Anal. Calc'd. for C$_{15}$H$_{16}$O$_5$: C, 65.21; H, 5.84. Found: C, 65.23; H, 5.78.

EXAMPLE 10

Khellinone (Formula B-7)

Refer to Chart B

A methylene chloride solution (25 ml) of the formula B-6 product of Example 9 (1.0 g) is added to a methylene chloride solution (100 ml) saturated with anhydrous hydrogen bromide at $-15°$ C. After stirring for 15 minutes, thin-layer chromatography (15% ethyl acetate/Skellysolve-B) indicates the reaction is complete. The reaction is poured into a saturated solution of sodium bicarbonate and the organic layer separated, dried over magnesium sulfate and solvent removed, in vacuo, to give the pure title product.

Physical characteristics are as follows:

Melting point: 97.5°–100° C.

IR (cm$^{-1}$, mull): 2956, 2926, 2855, 1620, 1470, 1445, 1381, 1303, 1152 and 1080.

$^1$H-NMR ($\delta$, CDCl$_3$): 10.09, 7.50, 6.90, 4.13, 4.03 and 2.71.

Mass spectra (m/e): 236, 221, 206, 203, 191, 189, 175, 163, 119 and 43.

UV ($\lambda_{max}$, ethanol): 205, 251, 280 and 359.

EXAMPLE 11

Khellin (Formula B-8)

Refer to Chart B

Sodium hydride (1.1 g, 50% oil dispersion) is added to a flame-dried 125-ml round-bottom flask under nitrogen. The sodium hydride is washed three times with 25 ml of hexane, and tetrahydrofuran (25 ml) is added. The formula B-7 product from Example 10 (1.7 g) is dissolved in ethyl acetate (15 ml) and this solution is added in 2-ml portions to the sodium hydride suspension. Effervescence is noted but no generation of heat (exotherm) is measured during the 5-minute addition time. After approximately 10 minutes, a substantial generation of heat causes the solvent to reflux gently. After 0.5 hour, the reaction returns to room temperature and is poured into 50 ml of 2N hydrochloric acid and approximately 50 g of ice. Ethyl acetate (100 ml) is added and the organic layer separated. The aqueous mixture is extracted three times with 50 ml of ethyl acetate and the organic layers are combined, dried over magnesium sulfate, and solvent removed in vacuo to yield 2.15 g of crude title product. This material is washed three times with 10 ml of ether to yield 1.60 g of analytically pure title product.

EXAMPLE 12

1-(4-Hydroxy-6,7-dimethoxybenzo[b]furanyl)ethanone (Formula C-5)

Refer to Chart C

A solution of lead (IV) acetate (0.50 g) in a 1:1 mixture of methanol and trimethylorthoformate (5 ml) is added dropwise, over 2 minutes, to a solution of the formula A-6 (C-1) product of Example 5(A) (0.21 g) in a 1:1 mixture of methanol and trimethylorthoformate (5 ml). After stirring at room temperature for 1.5 hours, a second portion of lead (IV) acetate (0.05 g) in 1 ml of the 1:1 mixture of methanol and trimethylorthoformate is added, and the mixture stirred for an additional hour. The reaction mixture is poured into methylene chloride (100 ml) and saturated aqueous sodium bicarbonate (25 ml) with vigorous stirring. The layers are separated and the aqueous phase is extracted three times with 5 ml of methylene chloride. The organic layers are combined, dried over sodium sulfate, filtered, and evaporated, affording 300 mg of the formula C-3 compound. This material is dissolved in methylene chloride (25 ml) and three small crystals (approx. 5 mg) of para-toluenesulfonic acid added. After 0.5 hour, the reaction mixture is applied directly to 20 g of silica gel and eluted with methylene chloride to afford an impure title product. Chromatography over 20 g of silica gel, and elution with 25% ethyl acetate/Skellysolve-B affords 0.20 g of the title product.

Alternatively, a solution of thallium (III) nitrate trihydrate (3.11 g) in a 1:1 mixture of methanol and trimethylorthoformate (25 ml) is added dropwise, over 0.5 hour, to a solution of the formula A-6 (C-1) product of Example 5(A) (1.03 g) in a 1:1 mixture of methanol and trimethylorthoformate (50 ml). After stirring at room temperature for 2.5 hours, the reaction is poured into a mixture of methylene chloride (500 ml) and saturated aqueous sodium bicarbonate (50 ml) with vigorous stirring. The layers are separated and the aqueous phase is extracted twice with 20 ml of methylene chloride. The organic layers are combined, dried over magnesium sulfate, filtered, and evaporated to afford 1.23 g of the formula C-3 compound. This material is dissolved in methylene chloride (25 ml) and para-toluenesulfonic acid (100 mg) added. After stirring at room temperature for 2.5 hours, the solvent is removed, in vacuo, at 40° C. and the product is chromatographed over 125 g of silica gel, eluting with 25% ethyl acetate/Skellysolve-B, to yield 0.90 g of the title product.

EXAMPLE 13

1-(4,6,7-Trimethoxy-5-benzofuranyl)ethanone
(Formula C-6)

Refer to Chart C

In a flame-dried flask under nitrogen, the formula C-5 product of Example 12 (0.240 g), 1,4,7,10,13,16-hexaoxacyclooctadecane (18-crown-6) (0.024 g), potassium carbonate (0.3 g), dimethyl sulfate (0.14 g), and tetrahydrofuran (10 ml, anhydrous) are brought to reflux. After 4 hours, the reaction is cooled to room temperature and poured into a stirred mixture of methylene chlorie (50 ml) and water (25 ml). The layers are separated and the aqueous phase is extracted three times with 10 ml of methylene chloride. The organic phases are combined, dried over sodium sulfate, filtered, and evaporated to afford 0.310 g of crude product. Flash chromatography over silica gel (25 g, 10% ethyl acetate/Skellysolve-B) affords 0.232 g of the title product.

The product obtained in this example is identical to a previously prepared standard by comparison of NMR, IR, Mass spectra, and mobility on thin-layer chromatography (10% ethyl acetate/Skellysolve-B).

EXAMPLE 14

1-(6-Hydroxy-4,7-dimethoxy-5-benzofuranyl)ethanone
(Formula C-7)

Refer to Chart C

A solution of the formula C-6 product of Example 13 (0.250 g) in methylene chloride (5 ml) is cooled to 0° C. Boron trifluoride etherate (1.0 ml) is added dropwise and the ice bath removed. After 4 hours, the crude product is partitioned between water (10 ml) and methylene chloride (20 ml) and the layers are separated. The aqueous phase is extracted three times with 10 ml of methylene chloride, and the organic layers are combined, dried over magnesium sulfate, filtered, and evaporated to afford 0.31 g of an orange semisolid. Flash chromatography over 25 g of silica gel (10% ethyl acetate/Skellysolve-B) affords 0.176 g of the title product.

Alternatively, a solution of the formula C-6 product of Example 13 (0.250 g) in methylene chloride (2 ml) is cooled to 0° C. in flame-dried flask under nitrogen. Aluminum chloride (4.2 ml of 1.9M solution in nitrobenzene) is added dropwise and the ice bath removed. After 4.75 hours, the crude product is partitioned between water (10 ml) and methylene chloride (20 ml) and the layers are separated. The aqueous phase is extracted three times with 10 ml of methylene chloride and the organic layers are combined, dried over magnesium sulfate, filtered, and evaporated to afford 0.31 g of an orange semisolid. Flash chromatography over 25 g of silica gel (10% ethyl acetate/Skellysolve-B) affords 0.140 g of the title product.

The product obtained in this example is identical to a previously prepared standard by comparison of NMR, IR, Mass spectra, and mobility on thin-layer chromatography (10% ethyl acetate/Skellysolve-B).

EXAMPLE 15

A. 5-Butyl-7-methoxy-4-benzofuranol, acetate
(Formula D-4: X is oxygen; R is propyl)

Refer to Chart D

The formula A-5 (D-1) product of Example 4(A) (2.08 g) is added to a flame-dried flask under nitrogen. Anhydrous ethyl ether (200 ml) is added and the solution cooled to 0° C. with stirring. Propyl lithium (30 cc, 1M solution) is then added dropwise over 30 minutes and the resulting reaction stirred at 0° C. for four hours. The reaction is quenched by addition of a saturated solution of ammonium chloride followed by extraction with ether. The extract is dried with sodium sulfate and solvent removed in vacuo to yield the ketone of formula D-2.

The formula D-2 ketone (2.34 g) is added to amalgamated zinc (5 g) in concentrated hydrochloric acid (100 ml) and ethanol (100 ml) and heated to reflux for three hours. The reaction is cooled to room temperature and extracted with ether to yield the phenol of formula D-3.

The formula D-3 phenol (2.20 g) is added to an acetic anhydride/pyridine mixture (5 ml/50 ml) and stirred at room temperature for several hours. The reaction is poured into 2N hydrochloric acid and extracted with ether. The ether is dried and evaporated in vacuo to yield the formula D-4 compound.

B. 5-Butyl-7-methoxy-4-benzo(b)-thiophen-4-ol, acetate
(Formula D-4: X is sulfur; R is propyl)

Refer to Chart D

Utilizing a procedure similar to that described in Example 15(a), the formula A-5 (D-1) product of Example 4(B) is converted to the title product.

FORMULA CHART
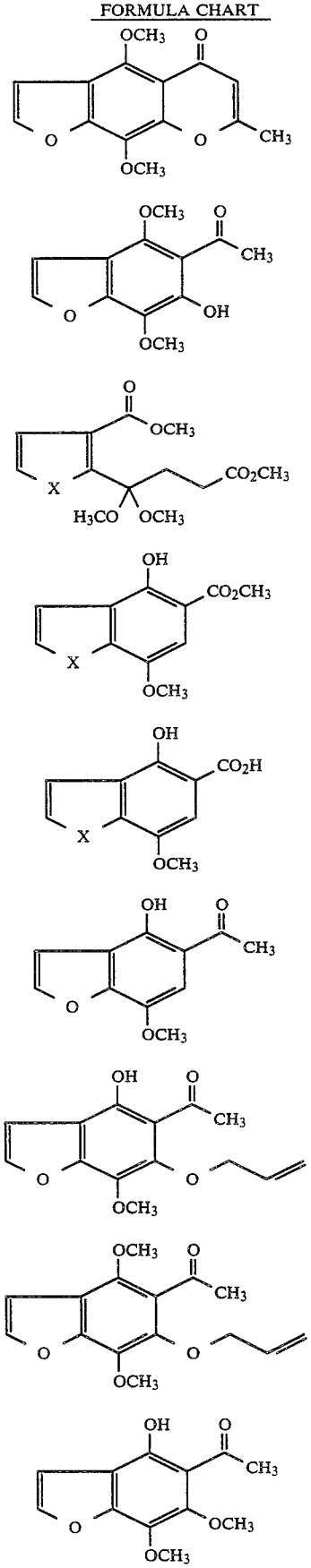
-continued
FORMULA CHART
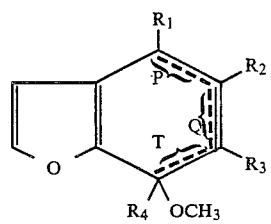   X
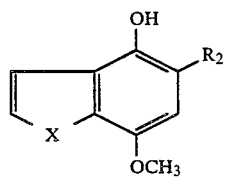
CHART A
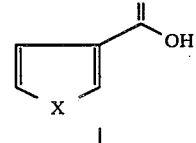   A-1
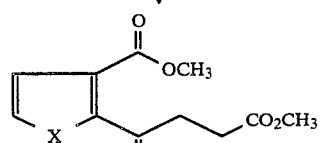   A-2
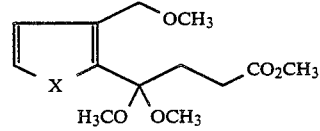   A-3
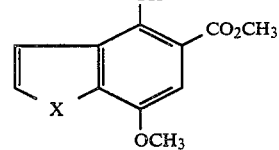   A-4
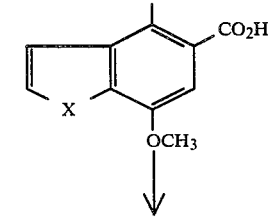   A-5

CHART A
-continued
A-6
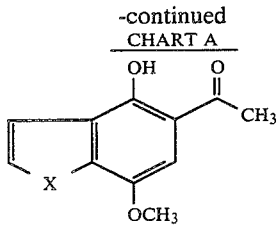
CHART B
B-8
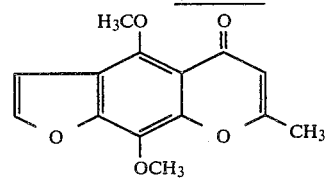
CHART B
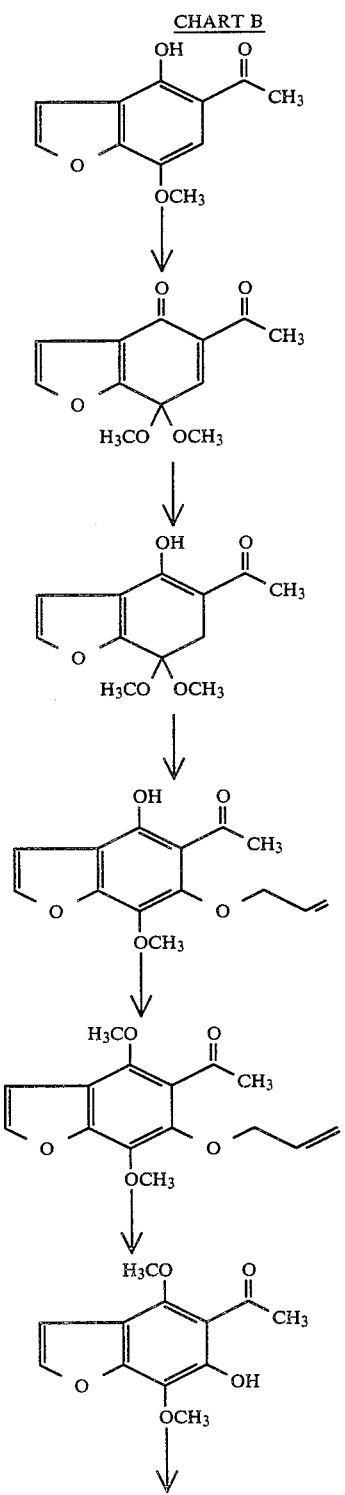
B-1(A-6)
B-2
B-3
B-5
B-6
B-7
CHART C
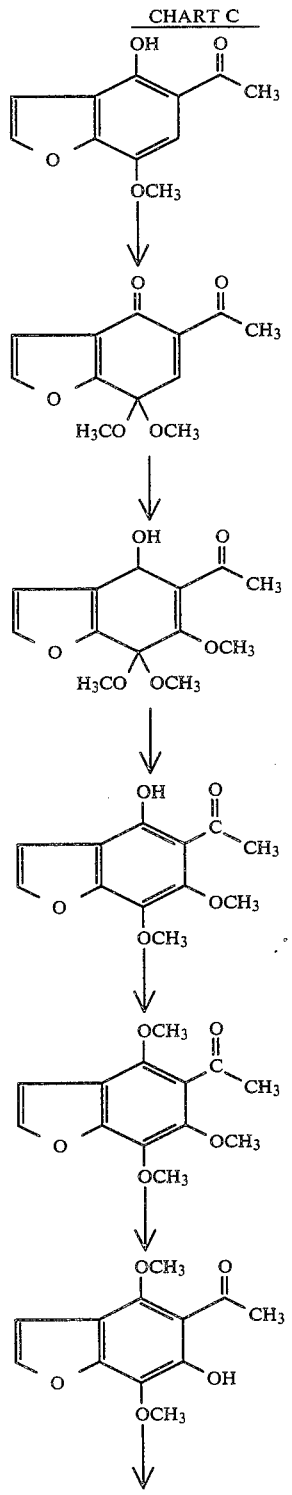
C-1(A-6)
C-2
C-3
C-5
C-6
C-7

-continued
CHART C

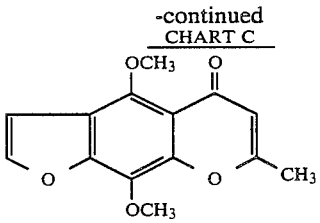
C-8

CHART D

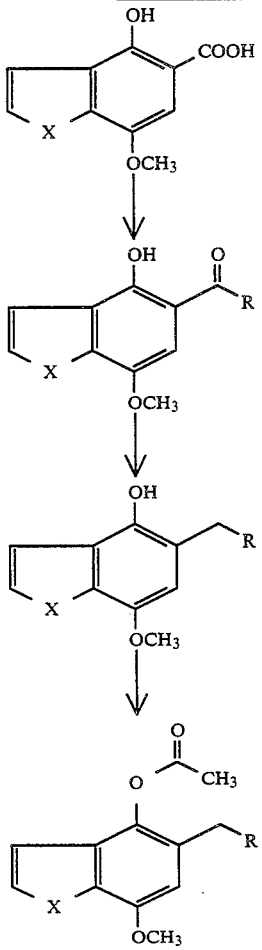

D-1(A-5)

D-2(A-6)

D-3

D-4

Compounds D-3 and D-4 are useful in the treatment of asthma. For example, these compounds are useful as bronchodilators or as inhibitors of mediators such as SRS-A which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations, by inhalation in the form of aerosols or solutions for nebulizers; or by insufflation in the form of powder. Doses in the range of about 0.01 to 50 mg per kg of body weight are used 1 to 4 times a day, the exact dose depending on the age, weight, and condition of the patient and on the frequency and route of administration. For the above use these compounds can be combined advantageously with other anti-asthmatic agents, such as sympathomimetics (isoproterenol, phenylephrine, ephedrine, etc.); xanthine derivatives (theophylline and aminophylline); and corticosteroids (ACTH and prednisolone).

These compounds are effectively administered to human asthma patients by oral inhalation or by aerosol inhalation.

For administration by the oral inhalation route with conventional nebulizers or by oxygen aerosolization it is convenient to provide the instant active ingredient in dilute solution, preferably at concentrations of about 1 part of medicament to form about 100 to 200 parts by weight of total solution. Entirely conventional additives may be employed to stabilize these solutions or to provide isotonic media, for example, sodium chloride, sodium citrate, citric acid, sodium bissulfite, and the like can be employed.

For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizers. Instead of a co-solvent there can also be used a dispensing agent such as oleyl alcohol. Suitable means to employ the aerosol inhalation therapy technique are described fully in U.S. Pat. No. 2,868,691 for example.

I claim:

1. A process for preparing a compound of the formula IV

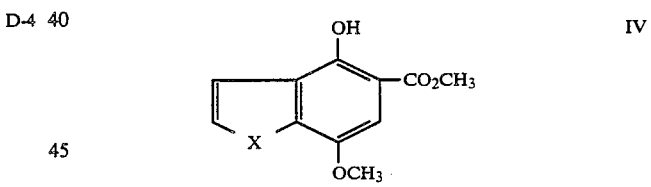

wherein X is
(a) —O—, or
(b) —S—;
which comprises: cyclizing a compound of the formula III

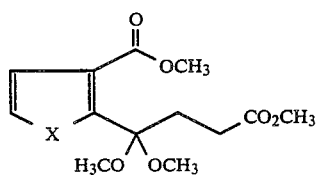

using a Dieckmann-type cyclization performed in the presence of potassium tert-butoxide in tetrahydrofuran at −80° to 0° C. and followed by treatment with anhydrous hydrochloric acid.

2. A compound of the formula III

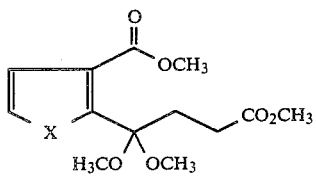
III
wherein x is
(a) —O—, or
(b) —S—.
3. 2-Furanbutanoic acid, γ,γ-dimethoxy-3-(methoxycarbonyl)-, methyl ester, a compound according to claim 2, wherein X is —O—.
4. Methyl, γ,γ-dimethoxy-3-methoxycarbonyl-2-thiophenebutanoate, a compond according to claim 2, wherein X is —S—.
* * * * *

UNITED STATES PATENT OFFICE
CERTIFICATE OF CORRECTION

Patent No. 4,609,739                    Dated 2 September 1986

Inventor(s)   R.B. Gammill

It is certified that error appears in the above-identified patent and that said Letters Patent are hereby corrected as shown below:

1st page, column 2, line 8: "A.E. Ebnother" should read --A. Ebnöther--.
Column 1, lines 14-15: "chenmical" should read --chemical--.
Column 1, line 35: "(1979)." should read --(1978).--.
Column 3, line 17: "A.E. Brother" should read --A. Ebnöther--.
Column 5, line 11: "(1979)" should read --(1974)--.
Column 7, line 46: "Raid" should read --Rapid--.
Column 15, line 44: "chlorie" should read --chloride--.
Column 18, line 17 (rt side of structure): "(blank)" should read --XI--.
Column 19, line 35: should read

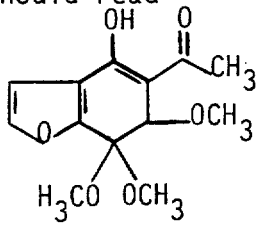

Signed and Sealed this

Sixteenth Day of December, 1986

Attest:

DONALD J. QUIGG

Attesting Officer          Commissioner of Patents and Trademarks